United States Patent
Okahara et al.

(10) Patent No.: US 6,905,799 B2
(45) Date of Patent: Jun. 14, 2005

(54) NONAQUEOUS ELECTROLYTIC SOLUTION AND SECONDARY BATTERY CONTAINING THE SAME

(75) Inventors: Kenji Okahara, Kanagawa (JP); Noriko Shima, Ibaraki (JP); Hitoshi Suzuki, Ibaraki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/030,143

(22) PCT Filed: May 25, 2001

(86) PCT No.: PCT/JP01/04406

§ 371 (c)(1),
(2), (4) Date: Sep. 20, 2002

(87) PCT Pub. No.: WO01/91223

PCT Pub. Date: Nov. 29, 2001

(65) Prior Publication Data

US 2003/0068561 A1 Apr. 10, 2003

(30) Foreign Application Priority Data

May 26, 2000 (JP) ........................................ 2000-155772

(51) Int. Cl.[7] ............................................... H01M 6/16
(52) U.S. Cl. ....................... 429/327; 429/326; 429/329; 429/231.1; 429/231.3; 429/231.4; 429/231.8
(58) Field of Search ................................. 429/327, 326, 429/329, 231.1, 231.3, 231.4, 231.8

(56) References Cited

U.S. PATENT DOCUMENTS 4,888,255 A  * 12/1989 Yoshimitsu et al. ........ 429/344

FOREIGN PATENT DOCUMENTS

| EP | 0296589 A2 | * 12/1988 |
| EP | 548660 | 6/1993 |
| GB | 2068631 | 8/1981 |
| JP | 54-35329 | 3/1979 |
| JP | 58-214281 | 12/1983 |
| JP | 62-86673 | * 4/1987 |
| JP | 62-110257 | * 5/1987 |
| JP | 7-235327 | 9/1995 |
| JP | 10-74537 | 3/1998 |
| JP | 10-112422 | 4/1998 |
| JP | 10-308236 | 11/1998 |
| JP | 2001-15172 | 1/2001 |

* cited by examiner

Primary Examiner—Laura Weiner
(74) Attorney, Agent, or Firm—Oblon, Spivak, McClelland, Maier & Neustadt, P.C.

(57) ABSTRACT

There are disclosed a non-aqueous electrolyte which comprises a non-aqueous organic solvent and a lithium salt, and further contains a compound represented by the following formula (I):

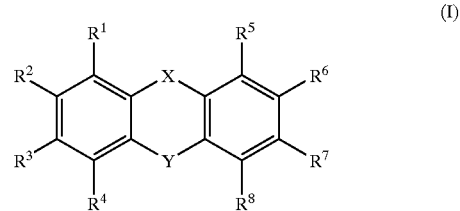

wherein X represents —O—, —S—, —CO— or —$SO_2$, Y represents a single bond, —$CH_2$—, —$CH_2$—$CH_2$—, —CH=CH— or —CO— and $R^1$ to $R^8$ each independently represent a hydrogen atom, an alkyl group, a phenyl group, or a halogen group, provided that X and Y do not represent —CO— at the same time.

4 Claims, 1 Drawing Sheet

NONAQUEOUS ELECTROLYTIC SOLUTION AND SECONDARY BATTERY CONTAINING THE SAME

TECHNICAL FIELD

This invention relates to a non-aqueous electrolyte and a secondary battery using the same.

PRIOR ART

In a recent trend of a small-sized and light weight electronic devices, a non-aqueous secondary battery using a carbon material capable of storing and releasing lithium in an anode and a lithium metal oxide in a cathode has been widely used as a power source of an electronic device for daily use, such as a portable video camera and computer, etc., since it has a high voltage, a high energy density and an excellent storing property. The non-aqueous secondary battery exhibiting a function of a battery by storing and releasing lithium ions as such is called lithium ion secondary battery, on which research and development have been active and competition for commercialization of which has been activated. In addition, a lithium ion secondary battery has been drawing attention, which has a large capacity and a high energy density, in addition, being a closed type, requiring no maintenance, for the purpose of an electric car from an environmental point of view, and load leveling of electric power demand, etc.

As an electrode-active material for a cathode of the lithium ion secondary battery, layered lithium cobalt oxide ($LiCoO_2$), lithium nickel oxide ($LiNiO_2$), etc. have been mainly used, due to their large capacities per unit weight, however, they have serious drawbacks as follows. That is, those lithium metal oxides become extremely unstable in an overcharged state (in which lithium ions are completely left), causing a rapid heat-generating reaction with an electrolyte, a precipitation of lithium on an anode, and in the worst case, causing an explosion and fire.

In order to solve such problems, there have been proposed an attempt that a little amount of aromatic compound is added to an electrolyte of a lithium ion secondary battery as an additive, to secure safety against overcharging of a battery, for example, in Japanese Provisional Patent Publications Nos. Hei. 7-302614 (1995), Hei. 9-50822 (1997) and Hei. 9-106835 (1997), Japanese Patent No. 2939469, etc.

Further, in Japanese Patent No. 2983205, prevention of overcharging by an addition of diphenyl ether, etc. has been proposed.

In Japanese Provisional Patent Publications Nos. Hei. 7-302614 (1995) and Hei. 9-50822 (1997), it is proposed to use an organic compound with a low molecular weight of 500 or less, such as an anisole derivative having a π electron orbital which has a reversible reduction-oxidation potential at a higher (more noble) potential than that of a cathode of the fully charged secondary battery, in an electrolyte as an additive. It is thought that protection mechanism is established by the additive, through an action known as red-ox shuttle, consuming an overcharged electric current in an overcharging state.

In Japanese Provisional Patent Publication No. Hei. 9-106835 (1997), it is proposed to elevate an internal voltage of the battery, through polymerization of additives in an electrolyte at a voltage of the battery higher than the maximum working voltage of the battery, in order to protect a battery when it is frequently overcharged.

In Japanese Patent No. 2939469, it is proposed to add a terphenyl derivative having a particular structure into a solvent of an electrolyte. It is stated that this additive starts a polymerization reaction at a voltage in an overcharging state, generating a polymer acting as a resistance and which is hard to be resolved, and effectively functions against overcharging.

However, although the anisole derivative proposed in Japanese Provisional Patent Publications Nos. Hei. 7-302614 (1995) and Hei. 9-50822 (1997) actually functions as a red-ox shuttle in an overcharging state, it was found that it yields to a reaction in a voltage range of a normal battery use, whereby lowering a discharge capacity, and causing an unfavorable influence on a recycling property and a storing property.

In addition, the biphenyl proposed in Japanese Provisional Patent Publication No. Hei. 9-106835 (1997) has an effect for preventing overcharging, however, it was found that it has an unfavorable influence on an output property of the battery. Further, it was found that 3-chlorothiophene and furan are vulnerable to an oxidative decomposition, which yields to an oxidation reaction under conditions of a normal battery use, having an unfavorable influence on a battery property.

The terphenyl derivative proposed in Japanese Patent No. 2939469 has polymerization reactivity, however, it was found to lower a battery performance since it has a high molecular weight and is not easily dissolved in an electrolyte.

Further, the diphenyl ether in Japanese Patent No. 2983205 has a strong stimulating odor, causing a problem in handling as an additive.

Therefore, a non-aqueous electrolyte and a secondary battery have been sought for, which can substantially prevent an overcharging of a battery without causing an adverse influence on a battery property under conditions for a normal use, and which are free from a problem of stimulating odor.

DISCLOSURE OF THE INVENTION

The present inventors have made intensive studies to solve the above-mentioned problems, and have found that the above-mentioned problems can be solved by adding a compound with a particular structure to an electrolyte, and thus have completed the invention. The present invention is summarized in the following sections (1) to (7).

(1) A non-aqueous electrolyte which comprises a non-aqueous organic solvent and a lithium salt, and further contains a compound represented by the following formula (I):

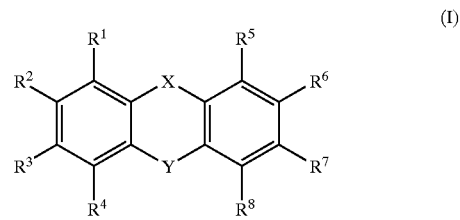

wherein X represents —O—, —S—, —CO— or —$SO_2$, Y represents a single bond, —$CH_2$—, —$CH_2$—$CH_2$—, —CH=CH— or —CO— and $R^1$ to $R^8$ each independently represent a hydrogen atom, an alkyl group, a phenyl group, or a halogen group, provided that X and Y do not represent —CO— at the same time.

(2) The non-aqueous electrolyte according to the above (1), wherein X represents —O—, —S— or —CO— and Y represents a single bond, —CH$_2$—CH$_2$—, —CH=CH— or —CO— (provided that X and Y do not represent —CO— at the same time).

(3) The non-aqueous electrolyte according to the above (1), wherein X represents —O— or —S— and Y represents a single bond or —CO—.

(4) The non-aqueous electrolyte according to the above (1), wherein X represents —O— and Y represents a single bond.

(5) The non-aqueous electrolyte according to the above (1), wherein X represents —CO— and Y represents a single bond, —CH$_2$—CH$_2$— or —CH=CH—.

(6) The non-aqueous electrolyte according to any one of the above (1) to (5), wherein the compound represented by the formula (I) is contained in the electrolyte in an amount of 0.01 to 0.8 mmol/g.

(7) The non-aqueous electrolyte according to any one of the above (1) to (6), wherein it is an electrolyte for a non-aqueous secondary battery comprising a cathode containing a lithium metal complex oxide and an anode containing a material which is capable of storing and releasing lithium.

Further, as the other embodiments of the present invention, the following (8) to (11) can be mentioned.

(8) A non-aqueous secondary battery which is equipped with a cathode containing a lithium metal complex oxide, an anode containing a material which is capable of storing and releasing lithium and the electrolyte according to any one of the above (1) to (7).

(9) A non-aqueous secondary battery which is equipped with a cathode containing a lithium metal complex oxide, an anode containing a material which is capable of storing and releasing lithium and an electrolyte, wherein the cathode comprises the compound represented by the formula (I) according to any one of the above (1) to (5).

(10) The non-aqueous secondary battery according to the above (8) or (9), wherein the lithium metal complex oxide is a lithium cobalt oxide, lithium nickel oxide and/or lithium manganese oxide.

(11) The non-aqueous secondary battery according to any one of the above (8) to (10), wherein the material which is capable of storing and releasing lithium is a carbonaceous material.

BEST MODE FOR CARRYING OUT THE INVENTION

Figure 1:
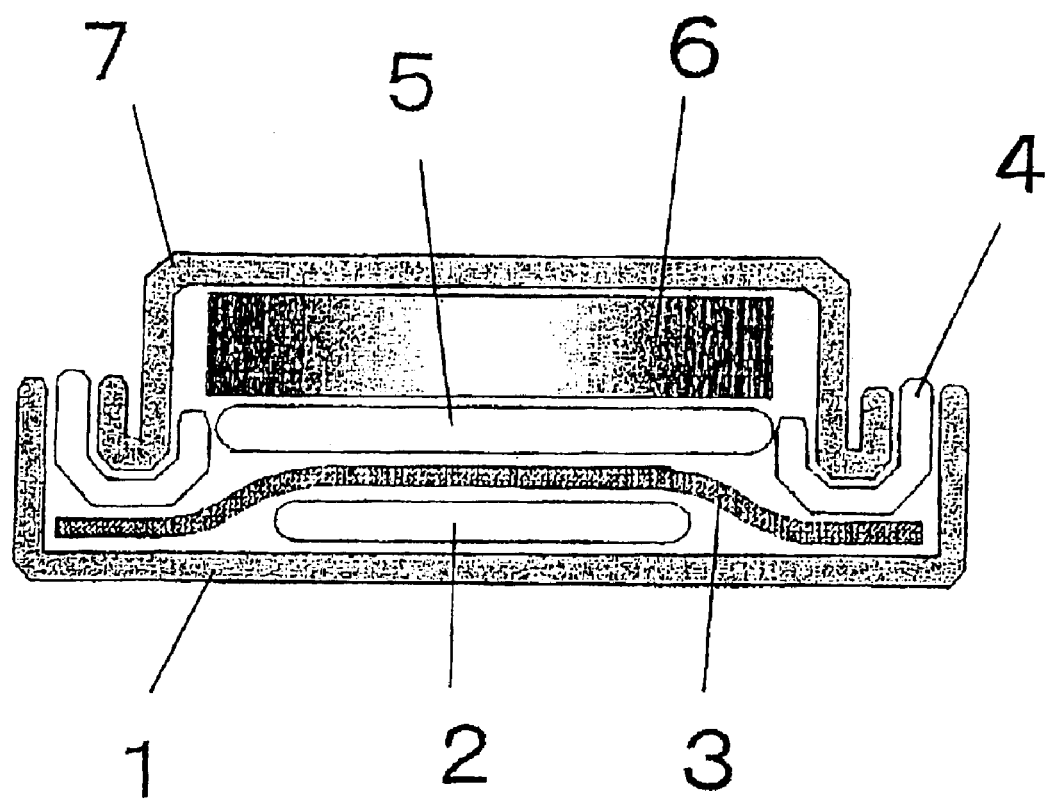
FIG. 1 is a sectional view showing an example of a structure of a coin cell battery, wherein reference numeral 1 represents a cathode can, 2 represents a cathode, 3 represents a separator, 4 represents a gasket, 5 represents an anode, 6 represents a spacer, and 7 represents an anode can.

In the present invention, it is essential that a compound represented by the following formula (I):

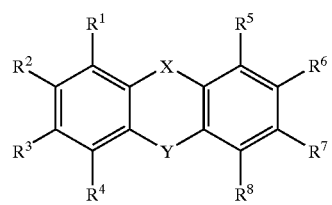

(I)

wherein X represents —O—, —S—, —CO— or —SO$_2$,
Y represents a single bond, —CH$_2$—, —CH$_2$—CH$_2$—, —CH=CH— or —CO— and R$^1$ to R$^8$ each independently represent a hydrogen atom, an alkyl group, a phenyl group, or a halogen group, provided that X and Y do not represent —CO— at the same time,
is contained in a non-aqueous electrolyte.

In the present invention, a compound wherein X represents —O—, —S— or —CO— and Y represents a single bond, —CH$_2$—CH$_2$—, —CH=CH— or —CO— (provided that X and Y do not represent —CO— at the same time) is preferred, and a compound wherein X represents —O— or —S— and Y represents a single bond or —CO, and a compound wherein X represents —O— and Y represents a single bond are more preferred, and the most preferred is a compound wherein X represents —O— and Y represents a single bond.

Specifically, preferred are dibenzofuran, xanthone, dibenzothiophene, thioxanthen-9-one,, 9-fluorenone, dibenzosuberone, dibenzosuberenone, etc. More preferred are dibenzofuran, xanthone, dibenzothiophene, thioxanthen-9-one, and particularly preferred is dibenzofuran. These compounds may have one or more substituents at the phenyl ring portion, selected from the group consisting of an alkyl group, a phenyl group and a halogen group.

Concentration of the compound represented by the above formula (I) to be contained in an electrolyte in the present invention is preferably from 0.01 mmol/g to 0.8 mmol/g, more preferably from 0.05 mmol/g to 0.5 mmol/g, and particularly preferably from 0.1 mmol/g to 0.3 mmol/g. When the concentration is lower than the above range, an effect for preventing overcharging is lowered, and when it is excessive, a normal battery property is adversely influenced.

There is no limitation for the non-aqueous organic solvent to be used in the present invention, and any known organic solvent can be used. For example, carbonates, ethers, ketones, sulfolane compounds, lactones, nitriles, halogenated hydrocarbons, amines, esters, amides, phosphate compounds, etc. can be used. As an representative examples, there are enumerated propylene carbonate, ethylene carbonate, chloroethylene carbonate, trifluoropropylene carbonate, diethyl carbonate, dimethyl carbonate, ethyl methyl carbonate, diisopropyl carbonate, vinylene carbonate, tetrahydrofuran, 2-methyltetrahydrofuran, 1,4-dioxane, 4-methyl-2-pentanone, 1,2-dimethoxyethane, 1,2-diethoxyethane, γ-butyrolactone, 1,3-dioxolane, 4-methyl-1,3-dioxolane, diethyl ether, sulfolane, methylsulfolane, acetonitrile, propionitrile, benzonitrile, butyronitrile, valeronitrile, 1,2-dichloroethane, dimethylformamide, dimethylsulfoxide, trimethyl phosphate, triethyl phosphate, etc., which may be used solely or as a mixed solvent of two or more kinds.

In the present invention, a solvent with a high permittivity is preferably contained in order to dissociate electrolytes. In this case, the solvent with a high permittivity means a compound having a specific permittivity of 20 or higher at 25° C. Among the solvent with a high permittivity, preferred are ethylene carbonate, propylene carbonate and compounds in which a hydrogen atom thereof is substituted with a halogen atom or an alkyl group. A ratio of the compound with a high permittivity to be contained in the electrolyte is preferably 20% by weight or more, more preferably 30% by weight or more, and most preferably 40% by weight or more.

As a preferably used solvent to be mixed with the solvent with a high permittivity, there are listed solvents with low viscosity including a linear carbonate such as dimethyl carbonate, diethyl carbonate, ethyl methyl carbonate, etc. and a linear ether such as 1,2-dimethoxy ethane, 1,2- diethoxy ethane, dimethoxy methane, etc., and they may be used singly or in combination of two or more kinds.

As a lithium salt to be used in the present invention, known lithium salts are listed. Specifically, there are mentioned lithium salts such as $LiClO_4$, $LiAsF_6$, $LiPF_6$, $LiBF_4$, $LiB(C_6H_5)_4$, LiCl, LiBr, $LiCH_3SO_3$, $LiCF_3SO_3$, $LiN(SO_2CF_3)_2$, $LiN(SO_2C_2F_5)_2$, $LiC(SO_2CF_3)_3$, $LiN(SO_3CF_3)_2$, etc., which may be used solely or in combination of two or more kinds.

Among the above, $LiBF_4$ and/or $LiPF_6$ are preferably used.

To the non-aqueous electrolyte of the present invention, known additive may be added, as long as it does not impair the effect of the present invention. For example, additives which substantially prevent decomposition of the electrolyte on a surface of an anode, thereby enabling an efficient charge and discharge of lithium ions, or additives generating an excellent film that is hard to be destroyed by dissolution and decomposition, maybe added to the above-mentioned electrolyte.

As a material for an anode which comprises a substance capable of storing and releasing lithium ions, constituting the battery of the present invention, those containing a substance capable of storing and releasing lithium ions as an active substance may be used. Among them, those containing a carbonaceous material are preferred. Specific examples of the carbonaceous material include, for example, a thermally degraded organic compounds in various pyrolysis conditions, artificial graphite, natural graphite, etc. Preferably used are artificial graphite prepared by heat-treating an easily graphitized pitch from various kinds of starting material at a high temperature, and other artificial graphite and purified natural graphite including Meso Carbon Micro Beads, graphitized mesophase-pitch-paste carbon fiber, and materials obtained by surface-treating those graphites in various ways including pitch.

For those carbonaceous materials, preferred are those having d value (distance between layers) of a lattice plane (002 face) obtained by X-ray diffraction according to the method of the Japan Society for Promotion of Scientific Research, within the range of 0.335 to 0.34 nm, more preferably, 0.335 to 0.337 nm. Ash content is preferably 1% by weight or less, more preferably 0.5% by weight or less, and particularly preferably 0.1% by weight or less. Size of the crystallite (Lc) obtained by X-ray diffraction according to the method of the Japan Society for Promotion of Scientific Research is preferably 30 nm or more, more preferably 50 nm or more, and most preferably 100 nm or more.

Further to these carbonaceous materials, a material for an anode capable of storing and releasing lithium may be mixed and used. As a material for an anode other than carbonaceous material, which is capable of storing and releasing lithium, there are exemplified a metal oxide material such as tin oxide, silicon oxide, etc., lithium metal, and various kinds of lithium alloys. These materials for an anode may be used singly, or in combination of two or more.

A method for preparing an anode using these materials for an anode is not particularly limited. For example, the anode can be prepared by optionally adding a binder, a thickening agent, a conductive material, a solvent, etc. to the anode material to obtain a slurry, and coating it on a substrate of a current collector and drying it. Or, the anode material may be formed into a sheet electrode by rolling, or it may be formed into a pellet electrode by compression molding.

The binder to be used in preparation of an electrode is not particularly limited as long as it is a stable material for a solvent or an electrolyte to be used in preparation of an electrode. Specific examples include poly(vinylidene fluoride), poly(tetrafluoroethylene), styrene-butadiene rubber, isoprene rubber, butadiene rubber, etc.

As the thickening agent, carboxymethyl cellulose, methyl cellulose, hydroxymethyl cellulose, ethyl cellulose, polyvinyl alcohol, oxidized starch, phosphated starch, casein, etc. are exemplified.

As the conductive material, a metal material such as copper, nickel, etc. and a carbon material such as graphite, carbon black, etc. are listed.

As a material for the current collector for anode, metals such as copper, nickel, stainless, etc. are used, among which a copper foil is preferred since it is easily processed into a thin film, and it is less costly.

A material for a cathode containing lithium metal complex oxide, which constitutes the battery of the present invention, is not particularly limited as long as it is a material containing a lithium metal complex oxide as an active material. Preferred examples are lithium transition metal complex oxide such as lithium cobalt oxide, lithium nickel oxide, lithium manganese oxide, etc. Particularly preferred are those containing as an active material, a metal complex oxide essentially containing lithium and cobalt or nickel.

A preparation method for the cathode is not particularly limited, and it is prepared according to the above-mentioned method for preparing the anode. As to form thereof, the cathode can be prepared by optionally adding a binder, a conductive material, a solvent, etc. to the cathode material, mixing them, and coating it on a substrate of a current collector to give a sheet electrode, or it may be formed into a pellet electrode by compression molding.

As a material for the current collector of the cathode, metals such as aluminum, titanium, tantalum, etc., and an alloy thereof is used. Among these, aluminum or its alloy is especially preferred in terms of energy density, since they are lightweight.

A material and a form of a separator to be used in the battery of the present invention are not particularly limited. However, the material is preferably selected from those which are stable in the electrolyte and excellent in liquid-storing property. It is preferred to use porous sheet or unwoven fabric, etc. made of polyolefin such as polyethylene, polypropylene, etc.

A method for preparing the battery of the present invention comprising at least an anode, a cathode and a nonaqueous electrolyte is not particularly limited, and may be suitably selected from the methods conventionally employed.

Further, the form of the battery is not particularly limited, and it is possible to use a cylinder type in which sheet electrodes and a separator are formed in a spiral, a cylinder type with an inside-out structure in which pellet electrodes and a separator are combined, a coin type in which pellet electrodes and a separator are stacked, etc.

EXAMPLES

Next, the present invention will be explained in more detail by referring to Examples.
(Measurement for Battery)
(Preparation of a Cathode)

90% by weight of lithium cobalt dioxide ($LiCoO_2$) as a cathode active material, 5% by weight of acetylene black as a conductive material and 5% by weight of poly(vinylidene fluoride) (PVdF) as a binder were mixed in a solvent of N-methylpyrrolidone, to give a slurry, and then, this slurry was coated on one surface of a 20 μm thickness aluminum foil and dried. It was rolled out by a compressor, and die-cut by a punch with a diameter of 12 mm to give a cathode.

(Preparation of an Anode)

95% by weight of a graphite (plane distance of 0.336 nm) as an anode active material and 5% by weight of poly (vinylidene fluoride) (PVdF) as a binder were mixed in a solvent of N-methylpyrrolidone, to give a slurry, and then, this slurry was coated on one surface of a 20 μm copper foil and dried. It was rolled out by a compressor, and die-cut by a punch with a diameter of 12 mm to give an anode.

When a battery is constructed, a ratio of the weight of the cathode active material W(c) and the weight of the anode active material W(a) is in the range which will not cause precipitations of lithium metal on the anode opposed to a cathode from which lithium ions are released. Accordingly, Rq=Q(a) X W(a)/{Q(c) X W(c)} must be 1.0 or more, wherein Q(c) mAh/g represents an electric capacity per weight of the cathode active material, under condition corresponding to an initial charging condition of the battery, and Q(a) mAh/g represents an electric capacity per weight of the anode active material, when it occludes lithium at maximum without letting lithium metal precipitated. In the present Examples and Comparative Examples, W(c)/W(a) is set to satisfy the relation of $1.1 \leq Rq \leq 1.2$. Incidentally, Q(c) or Q(a) can be measured by setting a test cell, using a cathode or an anode as a working electrode and lithium metal as a counter electrode, in the same electrolyte as used in constituting a battery, and intermediated by a separator. That is, they are obtained as a capacity which the cathode can charge (release lithium ions from the cathode) or a capacity which the anode can discharge (occlude lithium ions in the anode), until the highest possible potential (voltage) of the cathode or the lowest possible potential (voltage) of the anode corresponding to the initial charging condition of the aimed battery system, under the lowest possible current density.

(Assembly of the Battery)

In a dry box under the argon atmosphere, a battery was prepared using 2032 type coin cell with a structure as shown in FIG. 1. That is, a cathode 2 was placed on a cathode can 1, and 25 μm porous polyethylene film was put thereon as a separator 3. It was pressed by a polypropylene gasket 4, and then, an anode 5 was placed, and a spacer 6 was put thereon for adjusting a thickness. An electrolyte was added and let it absorbed inside the battery, and then, an anode can 7 was mounted thereon to seal the battery. In the present Examples and Comparative Examples, a capacity of a battery is designed to be about 4.0 mAh, with the highest charging potential of 4.2V and the lowest discharging potential of 3.0V.

(Evaluation Method)

evaluation of the battery was carried out in an order of initial charging and discharging (confirmation of capacity)→ discharging rate measurement test→ full charging operation→ overcharging test.

Initial charging (confirmation of capacity) was carried out according to the constant current/voltage charging method, with the current of 1 C (4.0 mA) and the highest potential of 4.2V. Charging was terminated at a point where a current value reached 0.05 mA. Discharging was carried out until 3.0V with 0.2 C.

Discharging rate measurement test was carried out 2 cycles and all the charging was uniformly performed according to the constant current/voltage charging method (terminated at 0.05 mA), with the current of 1 C and the highest potential of 4.2V, and the discharging rate was set either at 0.2 C or at 1 C. Discharging was terminated at 3V.

Incidentally, as an index for evaluating the excellence of discharging rate property, the following equation was used.

1 C/0.2 C discharging rate=(1 C discharging capacity/0.2 C discharging capacity)×100 (%)

The bigger value means the better rate property.

Full charging operation was carried out according to the constant current/voltage charging method (terminated at 0.05 mA), with the highest potential of 4.2V.

Overcharging test was carried out with a current of 1 C, and terminated either at 4.99V or after 3 hours (whichever reached at first).

As an index for evaluating effect for preventing overcharging, an amount of residual Li in the cathode was determined by an elemental analysis, after disassembling the overcharged coin cell. When the composition of the cathode was represented as $Li_xCoO_2$, the bigger values for x (residual amount of Li at the cathode) means the higher effect for preventing overcharging, which means the overcharging is not proceeded.

Using the electrolytes shown in the following Examples and Comparative Examples, the aforementioned measurements for battery were carried out, and the results were compared. The results are shown in Table 1.

In these examples, x (residual amount of Li at cathode) was obtained from a molar ratio of actual Li to Co in the cathode obtained by an elemental analysis (ICP emission spectrometry). Incidentally, an amount of phosphorous (P) in the cathode was also determined from the same analysis, and assuming that those are originated from $LiPF_6$, and then, the molar amount of actual Li was obtained by subtracting molar amount of Li corresponding to $LiPF_6$ from the total molar amount of Li in the cathode.

Example 1

In a mixed solvent of ethylene carbonate (EC) and diethyl carbonate (DEC) with a volume ratio of 3:7, lithium phosphate hexafluoride ($LiPF_6$) was dissolved in a concentration of 1 mol/liter to give an electrolyte, and dibenzofuran was added thereto in a concentration of 0.15 mmol/g to give an electrolyte.

Comparative Example 1

The same electrolyte was used as in Example 1, except that dibenzofuran was not added thereto, that is, an electrolyte was used in which lithium phosphate hexafluoride ($LiPF_6$) was dissolved in a concentration of 1 mol/liter in a mixed solvent of ethylene carbonate (EC) and diethyl carbonate (DEC) with a volume ratio of 3:7.

Comparative Example 2

An electrolyte was used which was prepared in the same manner as in Example 1, except that biphenyl was added in place of dibenzofuran.

Example 2

An electrolyte was used which was prepared in the same manner as in Example 1, except that xanthone was added in place of dibenzofuran.

Example 3

An electrolyte was used which was prepared in the same manner as in Example 1, except that dibenzosuberone was added in place of dibenzofuran.

Example 4

An electrolyte was used which was prepared in the same manner as in Example 1, except that dibenzosuberenone was added in place of dibenzofuran.

Comparative Example 3

An electrolyte was used which was prepared in the same manner as in Example 1, except that 2,3-benzofuran was added in place of dibenzofuran.

TABLE 1

|  |  | Residual Li ratio x in $Li_xCoO_2$ in cathode | Rate property 1 C/0.2 C discharge ratio |
|---|---|---|---|
| Comp. Ex. 1 | No additive | 0.16 | 63% |
| Comp. Ex. 2 | biphenyl | 0.37 | 50% |
| Comp. Ex. 3 | 2,3-benzofuran | 0.23 | 77% |
| Example 1 | dibenzofuran | 0.35 | 61% |
| Example 2 | xanthone | 0.56 | 49% |
| Example 3 | dibenzosuberone | 0.29 | 72% |
| Example 4 | dibenzosubererone | 0.31 | 67% |

It was shown that Examples 1 to 4 had an effect of preventing overcharging, since their residual amounts of Li in cathode were large, as compared to Comparative Example 1 (blank) and Comparative Example 3. In addition, Examples 1, 3 and 4 exhibited almost the same effect for preventing overcharging as Comparative Example 2, and at the same time, they showed better rate properties than Comparative Example 2, so it was shown that they are well balanced. Further, Example 2 was shown to have a greater effect for preventing overcharging, since it had a larger residual amount of Li than Comparative Example 2.

INDUSTRIAL APPLICABILITY

According to the present invention, there can be provided a nonaqueous electrolyte and a secondary battery, which can substantially prevent an overcharging of the battery without causing an adverse influence on a battery property under the condition for a normal use, and which are free from a problem of stimulating odor.

What is claimed is:

1. A non-aqueous secondary battery which is equipped with a cathode containing a lithium metal complex oxide, an anode containing a material which is capable of storing and releasing lithium and an electrolyte which comprises a non-aqueous organic solvent and a lithium salt, and further contains a compound represented by the following formula (I):

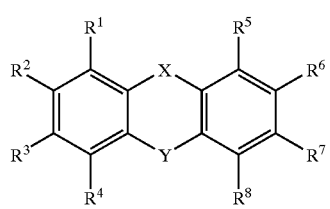

wherein X represents —O—, —S—, —CO— or —$SO_2$, Y represents a single bond, —$CH_2$—, —$CH_2$—$CH_2$—, —CH=CH— or —CO— and $R^1$ to $R^8$ each independently represent a hydrogen atom, an alkyl group, a phenyl group, or a halogen group, provided that X and Y do not represent —CO— at the same time, wherein the lithium metal complex oxide is a lithium cobalt oxide, lithium nickel oxide and/or lithium manganese oxide.

2. The non-aqueous secondary battery according to claim 1, wherein the material which is capable of storing and releasing lithium is a carbonaceous material.

3. A non-aqueous secondary battery which is equipped with a cathode containing a lithium metal complex oxide, an anode containing a material which is capable of storing and releasing lithium and an electrolyte which comprises a non-aqueous organic solvent and a lithium salt, and further contains a compound represented by the following formula (I):

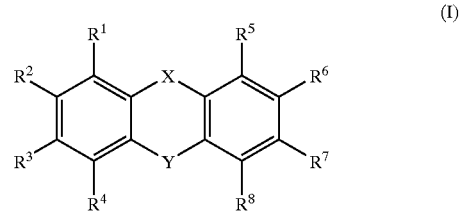

wherein X represents —O—, —S—, —CO— or —$SO_2$, Y represents a single bond, —$CH_2$—, —$CH_2$—$CH_2$—, —CH=CH— or —CO— and $R^1$ to $R^8$ each independently represent a hydrogen atom, an alkyl group, a phenyl group, or a halogen group, provided that X and Y do not represent —CO— at the same time, wherein the material which is capable of storing and releasing lithium is a carbonaceous material.

4. A non-aqueous electrolyte which comprises a non-aqueous organic solvent and a lithium salt, and further contains a compound represented by the following formula (I):

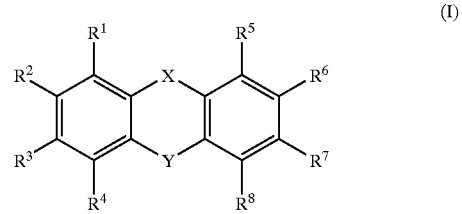

wherein X represents —O—, Y represents a single bond, and $R^1$ to $R^8$ each independently represent a hydrogen atom, an alkyl group, a phenyl group, or a halogen group.

* * * * *